US00PP17957P2

(12) United States Plant Patent
Heuger

(10) Patent No.: US PP17,957 P2
(45) Date of Patent: Aug. 28, 2007

(54) ***HELLEBORUS* PLANT NAMED 'HGC JOSHUA'**

(50) Latin Name: *Helleborus niger*
Varietal Denomination: HGC Joshua

(76) Inventor: Josef Heuger, Münsterstrasse 46, 49219 Glandorf (DE)

( * ) Notice: Subject to any disclaimer, the term of this patent is extended or adjusted under 35 U.S.C. 154(b) by 0 days.

(21) Appl. No.: 11/358,858

(22) Filed: Feb. 17, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Helleborus* plant named 'HGC Joshua', characterized by its compact and upright plant habit; dark green-colored leaves; and white to light green-colored flowers.

1 Drawing Sheet

Botanical designation: *Helleborus niger.*
Cultivar denomination: 'HGC Joshua'.

BACKGROUND OF THE INVENTION

The present Invention relates to a new and distinct cultivar of *Helleborus* plant, botanically known as *Helleborus niger,* and hereinafter referred to by the cultivar name HGC Joshua.

The new *Helleborus* is a product of a planned breeding program conducted by the Inventor in Glandorf, Germany. The objective of the breeding program was to create new early and long-flowering *Helleborus* cultivars with a good plant habit and have attractive flower coloration.

The new *Helleborus* originated from a cross-pollination made by the Inventor in December, 1999 in Glandorf, Germany of two unnamed proprietary seedling selections of *Helleborus niger,* not patented. The new *Helleborus* was discovered and selected by the Inventor as a flowering plant within the progeny of the stated cross-pollination in a controlled environment in Glandorf, Germany.

Asexual reproduction of the new cultivar by divisions at Glandorf, Germany since May, 2002, has shown that the unique features of this new *Helleborus* are stable and reproduced true to type in successive generations.

SUMMARY OF THE INVENTION

Plants of the cultivar HGC Joshua have not been observed under all possible environmental conditions. The phenotype may vary somewhat with variations in environment such as temperature and light level without, however, any variance in genotype.

The following traits have been repeatedly observed and are determined to be the unique characteristics of 'HGC Joshua'. These characteristics in combination distinguish 'HGC Joshua' as a new and distinct cultivar of *Helleborus:*

1. Compact and upright plant habit.
2. Dark green-colored leaves.
3. White to light green-colored flowers.

Plants of the new *Helleborus* flower earlier than plants of the parent selections.

Plants of the new *Helleborus* can be compared to the *Helleborus niger* cultivar HGC Josef Lemper, disclosed in U.S. Plant Pat. No. 15,615. In side-by-side comparisons conducted in Glandorf, Germany, plants of the new *Helleborus* differed from plants of the cultivar HGC Josef Lemper in the following characteristics:

1. Plants of the new *Helleborus* were more compact than plants of the cultivar HGC Josef Lemper.
2. Plants of the new *Helleborus* had shorter leaf petioles than plants of the cultivar HGC Josef Lemper.
3. Plants of the new *Helleborus* had smaller leaves than plants of the cultivar HGC Josef Lemper.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Helleborus*. The photograph comprises a side perspective view of a typical flowering plant of 'HGC Joshua' grown in a container.

DETAILED BOTANICAL DESCRIPTION

The aforementioned photographs, following observations and measurements describe plants grown in Glandorf, Germany, in a glass-covered greenhouse during the winter and in an outdoor nursery during the summer. Plants were grown in 13-cm containers and were about one year-old when the photographs and description were taken. During the production of the plants in the greenhouse, day temperatures were about 12° C. and night temperatures ranged from about 2° C. to about 12° C. During the production of the plants in the outdoor nursery, day temperatures ranged from about 5° C. to about 34° C. and night temperatures ranged from about 1° C. to about 25° C. In the following description, color references are made to The Royal Horticultural Society Colour Chart, 2001 Edition, except where general terms of ordinary dictionary significance are used.

Botanical classification: *Helleborus niger* cultivar HGC Joshua.

Parentage:

*Female parent.*—Unnamed proprietary seedling selection of *Helleborus niger,* not patented.

*Male parent.*—Unnamed proprietary seedling selection of *Helleborus niger,* not patented.

Propagation:

*Type.*—By divisions.

*Time to initiate roots, winter.*—About 56 days at 12° C.

*Time to produce a rooted plant, winter.*—About six months at 12° C. to 15° C.

*Root description.*—About 3 to 15 thick fleshy roots; non-branching; white to brown in color.

Plant description:

*Plant form/habit.*—Compact and upright plant habit; moderately vigorous growth habit. Leaves basal. Single flower form.

*Plant height.*—About 8 cm to 12 cm.

*Plant width* (*spread*).—About 20 cm to 25 cm.

*Foliage description.*—Arrangement: Basal; palmately compound with five to seven leaflets per leaf. Leaflet length: About 3.5 cm to 6 cm. Leaflet width: About 1.5 cm to 3 cm. Shape: Lanceolate; pedate. Apex: Broadly acuminate. Base: Acute. Margin: Serrate. Texture, upper and lower surfaces: Smooth, glabrous; leathery. Venation pattern: Pinnate; reticulate. Color: Developing and fully expanded leaflets, upper surface: Close to 147A; venation, 146B. Developing and fully expanded leaflets, lower surface: Close to 147B; venation, 146C. Petiole: Length: About 1 mm to 8 mm. Diameter: About 2 mm to 2.5 mm. Texture, upper and lower surfaces: Smooth, glabrous. Color, upper and lower surfaces: 146C to 146D; random spots, 200A to 200B.

Flower description:

*Flower type/habit.*—Single rounded flowers arranged singly on upright peduncles; flowers face mostly upright to outwardly; petals inconspicuous. Freely flowering habit with about 10 to 15 flowers developing per plant over the flowering period. Fragrance: Slightly fragrant.

*Natural flowering season.*—Long flowering period; intermittent flowering from November to February in Germany. Flowers persistent.

*Postproduction longevity.*—Flowers last about ten days on the plant.

*Flower buds.*—Height: About 1.2 cm. Diameter: About 8 cm. Shape: Ovoid. Color: 145D.

*Flowers.*—Diameter: About 4 cm to 5.5 cm. Depth: About 1.5 cm.

*Sepals.*—Quantity/arrangement per flower: Typically five to eight in a single whorl. Length: About 2.5 cm to 3 cm. Width: About 2 cm. Shape: Broadly ovate. Apex: Rounded acute. Margin: Entire. Texture, upper and lower surfaces: Smooth, glabrous; satiny. Color: Developing sepals, upper and lower surfaces: More white and brighter than 155D; towards the base, 144B. Fully expanded sepals, upper and lower surfaces: More white and brighter than 155D; towards the base, 144C; color becoming closer to 144B to 144C with development.

*Peduncles.*—Length: About 10 cm to 25 cm. Diameter: About 2 mm to 5 mm. Orientation: Mostly upright. Strength: Strong. Texture: Smooth, glabrous. Color: 145B; spots, 178A.

*Reproductive organs.*—Stamens: Quantity per flower: About 100. Anther shape: Oblong. Anther length: About 1 mm. Anther color: Close to 11A. Pollen amount: None observed. Pistils: Quantity per flower: About 15 to 20. Pistil length: About 1.3 cm to 1.4 cm. Stigma shape: Pointed. Stigma color: 145D. Style length: About 8 mm. Style color: 145D. Ovary color: 145C to 145D.

*Seed/fruit.*—Seed and fruit development have not been observed.

Disease/pest resistance: Plants of the new *Helleborus* have not been noted to be resistant to pathogens and pests common to *Helleborus*.

Temperature tolerance: When planted in the ground, plants of the new *Helleborus* have been observed to tolerate temperatures from about −10° C. to about 36° C.

It is claimed:

1. A new and distinct cultivar of *Helleborus* plant named 'HGC Joshua', as illustrated and described.

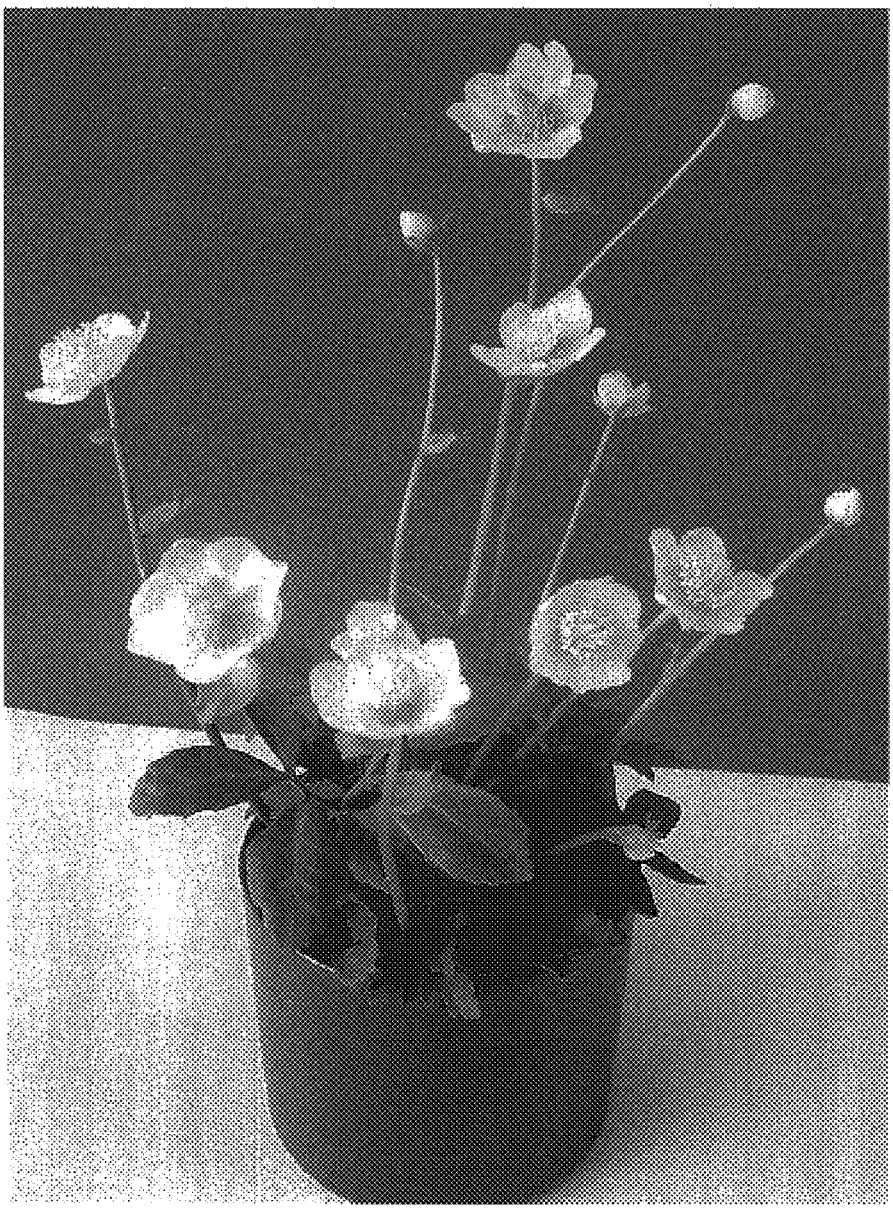

* * * * *